(12) United States Patent
Grodzki

(10) Patent No.: US 11,789,103 B2
(45) Date of Patent: Oct. 17, 2023

(54) OPTIMIZING AN MR CONTROL SEQUENCE

(71) Applicant: Siemens Healthcare GmbH, Erlangen (DE)

(72) Inventor: David Grodzki, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 134 days.

(21) Appl. No.: 17/460,733

(22) Filed: Aug. 30, 2021

(65) Prior Publication Data

US 2022/0065965 A1 Mar. 3, 2022

(30) Foreign Application Priority Data

Aug. 31, 2020 (DE) .................. 102020210981.8

(51) Int. Cl.
*A61B 5/00* (2006.01)
*G01R 33/54* (2006.01)
*A61B 5/055* (2006.01)
*G01R 33/561* (2006.01)

(52) U.S. Cl.
CPC .......... *G01R 33/543* (2013.01); *A61B 5/055* (2013.01); *G01R 33/5615* (2013.01)

(58) Field of Classification Search
CPC ... A61B 5/055; G01R 33/543; G01R 33/5615
See application file for complete search history.

(56) References Cited

U.S. PATENT DOCUMENTS

2013/0271139 A1* 10/2013 Grodzki ............... G01R 33/543
324/318
2015/0091567 A1 4/2015 Grodzki et al.

FOREIGN PATENT DOCUMENTS

DE 102013219754 A1 4/2015

OTHER PUBLICATIONS

Elster, Allen D.: "Slice-Select Rephasing"; in: Questions and Answers in MRI; URL: http://mriquestions.com/ss-gradient-lobes.html.
(Continued)

*Primary Examiner* — Joel F Brutus
(74) *Attorney, Agent, or Firm* — Banner & Witcoff Ltd.

(57) ABSTRACT

Method for optimizing an MR control sequence for acquiring MR data of an examination subject by means of an MR device having gradient coils. The method includes providing an MR control sequence having sequence portions, each having an excitation portion, a phase encoding portion and a readout portion, wherein the phase encoding portion is arranged in each case between the excitation portion and the readout portion with respect to time; providing a defined parameter for the MR control sequence; providing an optimization objective; ascertaining usage time of the gradient coils between the excitation portion and the readout portion with respect to time for each of the sequence portions; optimizing the excitation portions for each of the sequence portions considering the ascertained usage time for the corresponding sequence portion and the defined parameter with regard to the optimization objective; and providing the optimized MR control sequence having the optimized excitation portions.

14 Claims, 4 Drawing Sheets

(56) References Cited

OTHER PUBLICATIONS

Middione, Matthew J. et al: "Optimization methods for magnetic resonance imaging gradient waveform design"; NMR in Biomedicine, vol. 33; No. 12; pp. E4308; DOI: https://doi.org/10.1002/nbm.4308; 2020.
Elster, Allen D.: "Flow-Compensation"; in: Questions and Answers in MRI; URL: http://mriquestions.com/flow-compensation.html.
Office Action dated Jun. 25, 2021 for German Patent Application No. 102020210981.8.

* cited by examiner

OPTIMIZING AN MR CONTROL SEQUENCE

TECHNICAL FIELD

The disclosure relates to a method, an optimization unit, a magnetic resonance device, a computer program product and an electronically readable data medium for optimizing an MR control sequence.

BACKGROUND

In a magnetic resonance device, the body of an examination subject that is to be examined, in particular the body of a patient, is typically exposed to a relatively high main magnetic field, of 1.5 or 3 or 7 tesla for example, with the aid of a main magnet. In addition, gradient pulses are applied with the aid of a gradient coil unit. High-frequency radiofrequency pulses, for example excitation pulses, are then transmitted by means of suitable antenna devices via a radiofrequency antenna unit, which results in the nuclear spins of certain atoms excited into resonance by means of said radiofrequency pulses being tipped through a defined flip angle relative to the magnetic field lines of the main magnet field. During the relaxation of the nuclear spins, radiofrequency signals, referred to as magnetic resonance signals, are emitted, received by means of suitable radiofrequency antennas and then processed further. Finally, the desired image data can be reconstructed from the raw data acquired in the manner described.

To perform a particular measurement, it is therefore necessary to transmit a specific magnetic resonance control sequence (MR control sequence), also referred to as a pulse sequence, which consists of a series of radiofrequency pulses, for example excitation pulses and refocusing pulses, as well as, fitted thereto, gradient pulses that are to be transmitted in a coordinated manner in different gradient axes along different spatial directions. Readout windows, aligned with respect to time to said pulses, are set which specify the time intervals in which the induced magnetic resonance signals (MR signals) are captured.

In many MR control sequences, a rapid succession of excitation pulses, gradient pulses and readout windows is advantageous in order to achieve an MR control sequence of short duration and/or image data of good quality. This is relevant in particular in the context of thoracic or cardiological examinations, which are limited by the patient's breath-hold ability and/or heartbeat, or in interventional MR imaging.

SUMMARY

The object underlying the disclosure is to disclose a particularly flexible method for optimizing an MR control sequence with regard to its time efficiency and/or gradient efficiency. The object is achieved by means of the features of the independent claims. Advantageous aspects are described in the dependent claims.

The disclosed method for optimizing an MR control sequence embodied to acquire MR data of an examination subject by means of a magnetic resonance device comprising gradient coils provides the following method steps:

a. providing an MR control sequence comprising at least two sequence modules, each having an excitation module, a phase encoding module and a readout module, wherein the phase encoding module is in each case arranged between excitation module and readout module with respect to time, b. providing at least one defined parameter for the MR control sequence, c. providing an optimization objective, d. ascertaining a usage time of the gradient coils between excitation module and readout module with respect to time for each of the at least two sequence modules, e. optimizing the excitation modules for each of the at least two sequence modules taking into account the ascertained usage time for the corresponding sequence module and the at least one defined parameter with regard to the optimization objective, f. providing the optimized MR control sequence comprising the optimized excitation modules.

MR data typically comprises the raw data that is to be acquired by means of an MR control sequence.

A sequence module is typically a temporal section of an MR control sequence which comprises at least one excitation module, a phase encoding module and a readout module. The excitation module comprises at least one radiofrequency pulse (RF pulse). The excitation module may comprise a slice selection gradient simultaneously with the RF pulse, as a result of which the excitation module can be embodied for selective excitation of a slice. The phase encoding module comprises at least one gradient pulse for phase encoding. The amplitude of the magnetic field gradient generated by the phase-encoding gradient pulse typically defines the spacing, at which spacing from the center of the raw data space MR data in the raw data space is acquired when the sequence module is applied. The phase encoding module may also comprise a gradient pulse generating a magnetic field gradient of zero amplitude. The phase encoding module embodied for acquiring MR data at the periphery of the raw data space is typically the phase encoding module having the greatest amplitude of all of the phase encoding modules included in the MR control sequence.

The readout module typically comprises readout windows during which an analog-to-digital converter (ADC) is active and/or is embodied for acquiring MR signals. In addition, the readout module typically comprises a readout gradient which can be used for spatial encoding in the readout direction.

A sequence module is preferably a self-contained section of an MR control sequence, according to which section a defined set of raw data having a defined contrast can be generated and/or acquired. A sequence module is preferably embodied in such a way that when the sequence module is executed, MR data is acquired along a line in the raw data space, in particular along a line defined by the phase encoding module, in particular in the readout direction.

The first sequence module may be embodied for example to generate and/or acquire first MR data at a first spacing from the center of the raw data space. The second sequence module may be embodied for example to generate and/or acquire second MR data at a second spacing from the center of the raw data space.

The number of sequence modules included in the MR control sequence that are necessary for acquiring MR data of a subregion, in particular of a slice of the examination region, preferably corresponds to the number of lines of the raw data space in the phase encoding direction.

The temporal succession of the RF pulses and/or gradient pulses and/or readout windows included in a sequence module typically defines the contrast of the image data to be reconstructed from the MR data.

The at least one defined parameter is preferably a parameter relating to the MR control sequence and/or relating to at least one of the at least two sequence modules. The at least one defined parameter preferably comprises a parameter which is invariable in the course of the optimization. The optimization objective preferably comprises a characteristic, which characteristic the optimized MR control sequence is to fulfill. The optimization objective can comprise a characteristic relating to the MR control sequence and/or the examination subject and/or the magnetic resonance device. The optimization objective can comprise a quantitative value and/or a qualitative value and/or an extreme value, in particular for one characteristic.

A magnetic resonance device typically comprises three gradient coils. Each of the three gradient coils is typically embodied to generate a magnetic field gradient in one spatial direction. The three gradient coils are typically embodied to generate magnetic field gradients in three spatial directions orthogonal to one another. Said three spatial directions orthogonal to one another are also referred to as physical axes. The gradient coils are driven in accordance with the gradient pulses provided by the sequence modules. The gradient pulses included in a sequence module can be generated parallel to the physical axes only in special cases, in particular by one of the three gradient coils. A gradient pulse included in a sequence module can typically be generated by more than one gradient coil, in particular when the examination region is not aligned parallel to the physical axes.

The usage time of the gradient coils between excitation module and readout module with respect to time for a sequence module is preferably defined by the duration of the longest magnetic field gradient to be generated by a gradient coil between the excitation module and the readout module. The period of time between the excitation module and the readout module preferably corresponds to the time starting after the end of the excitation module and ending with the start of the readout module. The temporal difference from period of time between the excitation module and the readout module and the usage time is preferably free from a magnetic field gradient to be generated by a gradient coil and/or the gradient pulses included in the sequence module can be shifted in time in such a way that, outside of the usage time, no use of a gradient coil is provided between the excitation module and the readout module. The usage time of the gradient coils is preferably ascertained separately for each of the at least two sequence modules. The usage time can be a measure for a utilization of the load capacity of the gradient coil unit by the sequence module.

During optimization of the excitation modules, it is typically ensured that the optimized excitation modules and/or the optimized sequence modules and/or the MR control sequence comprising the optimized excitation modules comply with the defined parameter and/or fulfill the optimization objective. The optimization of the excitation modules is typically carried out separately for each of the at least two sequence modules and/or taking into account the usage time ascertained for the respective sequence module of the at least two sequence modules. In particular, taking into account the optimization objective may comprise taking into account the usage times of the other of the at least two sequence modules. The optimization objective may also be dependent on the usage times ascertained for the at least two sequence modules. The optimization preferably comprises adapting the excitation module to a loading of the gradient coils resulting from the associated sequence module, in particular a loading of the gradient coil unit, in particular between the excitation module and the readout module. The optimization of the excitation module may comprise changing the shape and/or the duration of the RF excitation pulse and/or of the associated slice selection gradient.

Providing the optimized MR control sequence may comprise an activation of the magnetic resonance device and/or an acquisition of MR data using the optimized MR control sequence. Providing the optimized MR control sequence may comprise storing the at least two optimized excitation modules.

The advantage of the method according to the disclosure lies in the fact that the MR control sequence is optimized on a module-by-module basis as a function of the use of the gradient coils between excitation module and readout module. In particular, an MR control sequence optimized according to the disclosure is able to make more consistent use of the gradient coils. The MR control sequence optimized according to the disclosure may be of shorter duration than the original MR control sequence, resulting in a shorter examination of the examination subject and/or dispensing with the need for breath-holding in cardiological imaging, for example. Accordingly, the optimized MR control sequence can acquire MR data more efficiently. A great optimization potential exists in particular in the case of fluctuating use of the gradient coils between excitation module and readout module, i.e. in the case of fluctuating usage time between the sequence modules, and consequently a greatly improved achievement of an optimization objective. This is relevant in particular for MR control sequences in which the phase encoding module dominates the usage time, such as in asymmetric echoes and/or three-dimensional measurements, for example. Gradient-echo-based and/or True fast imaging with steady state precession (TrueFISP)-based MR control sequences in particular harbor great optimization potential and thus, for example, can achieve a high, particularly temporal, resolution as a result of the optimization.

An aspect of the method provides that the defined parameter comprises one of the following characteristics: echo time, repetition time, ratio of echo time to repetition time, slice thickness, slice position, slice orientation, slice profile, examination region, amplitude of a magnetic field gradient, flip angle to be generated by the excitation module. The echo time may correspond to the period of time between the start and/or the temporal middle of the excitation module and the start and/or the temporal middle of the readout module. The repetition time may correspond to the period of time between the start of two successive sequence modules and/or excitation modules in each case. The flip angle to be generated by the excitation module, in particular by the corresponding RF excitation pulse, may correspond to the angle through which the spins are tipped. The flip angle and/or the echo time and/or the repetition time and/or a ratio of echo time to repetition time typically affect the contrast of the image data to be reconstructed. Since dedicated contrasts are required for dedicated diagnoses, it can be helpful to define such parameters in advance and to take these into account in the course of the optimization, preferably to leave them invariable. The slice position, the slice orientation, the slice profile and/or the examination region are typically dependent individually on the examination subject and/or the actual examination. Parameters defined in such a way ensure a correct visualization of the examination region. The amplitude of a magnetic field gradient may correlate with a stimulation of the examination subject. A parameter defined in such a way may be advantageous for safety reasons.

An aspect of the method provides that the optimization objective relates to an SAR exposure of the examination subject and/or a total duration of the sequence module and/or a ratio of echo time to repetition time and/or an echo time and/or a repetition time and/or a flip angle generated by an excitation module and/or allocation of a specific duration for the excitation module and/or an extreme value for one of the cited optimization objectives. The specific absorption rate (SAR) is subject to regulatory limitations and correlates with the intensity of the RF pulses, in particular with the size of its generated flip angle, i.e. with the excitation modules. In order to comply with the regulatory limitations, it may be necessary for the MR control sequence to include artificial pauses. One optimization objective may comprise an average SAR exposure. The optimized excitation modules can be chosen in such a way that for example the SAR exposure resulting therefrom and/or an average SAR exposure fall below a threshold value and/or are lowered by a defined percentage. In particular, the optimization can be used to allocate a longer duration for the excitation module, which longer duration can be used for an optimized excitation module with lower SAR exposure and/or an optimized excitation module with a greater flip angle to be generated. The shorter the duration of a sequence module, the shorter is the duration of an MR control sequence and/or the examination of the examination subject. Special contrasts require particularly small and/or large echo times, repetition times and/or ratio of echo time to repetition time. An optimization objective of said type can accordingly optimize an image contrast. The optimization objective may also comprise achieving a balance between the cited characteristics and a balance between the advantages resulting therefrom.

An aspect of the method provides that providing the optimization objective comprises establishing the optimization objective, in particular determining an extreme value for an SAR exposure of the examination subject and/or a total duration of the sequence module and/or a ratio of echo time to repetition time and/or a flip angle to be generated by an excitation module and/or a permissible maximum loading and/or average loading of at least one component of the magnetic resonance device and/or the ascertained usage time for the at least two sequence modules. The component may comprise for example a gradient coil and/or a gradient amplifier and/or a power amplifier required for a radiofrequency coil. In particular, the optimization objective may be established as a function of the MR control sequence and/or individually as a function of the examination subject. Dedicated parameters and/or the type of MR control sequence, for example whether gradient-echo-based or spin-echo-based, can be taken into account in the process of establishing the optimization objective. This aspect enables a particularly flexible optimization of the MR control sequence as a function of an individual optimization objective, in particular as a function of the actual examination subject.

The usage times of the gradient coils are preferably ascertained for all sequence modules included in the MR control sequence. The period of time corresponding to the difference between the period of time between excitation module and readout module and the maximum ascertained usage time can be used for optimizing all the sequence modules included in the MR control sequence. An initially optimized RF excitation pulse included in the excitation module can be chosen in the course of the optimization in such a way that said initially optimized RF excitation pulse has the maximum permissible amplitude and the duration of the initially optimized RF excitation pulse is chosen in such a way that the necessary flip angle can be generated. An excitation module comprising said initially optimized RF excitation pulse is typically compatible with all of the sequence modules of the MR control sequence. Depending on the usage time of each sequence module, the initially optimized RF excitation pulse can be adjusted in terms of its duration in each case in such a way that the optimization objective can be fulfilled. If, for example, the optimization objective comprises minimizing the echo time and/or the ratio of echo time to repetition time, then a shortest possible excitation module and a shortest possible period of time between excitation module and readout module may be advantageous. In this case the initially optimized RF excitation pulse can be adjusted in terms of its duration in each case in such a way that all the sequence modules have the same temporal succession. In addition, the optimized excitation modules can be checked with regard to the permissibility of the SAR exposure for the examination subject and/or the average amplitude for the RF excitation pulses. If the optimization objective comprises reducing the SAR exposure of the examination subject and/or increasing the flip angle generated by the RF excitation pulse, the duration of the initially optimized RF excitation pulse can be extended while complying with the temporal succession as a function of the ascertained usage time for each sequence module. This can reduce the SAR exposure of the examination subject.

An aspect of the method provides that the optimization of the excitation module comprises selecting a new RF excitation pulse included in the excitation module and/or adjusting the duration of an RF excitation pulse included in the excitation module. The excitation module can be optimized taking into account a time-averaged loading of components of the magnetic resonance device. A result of ascertaining the usage time may be that the duration of the excitation module can be increased and/or reduced in the course of the optimization. The excitation module is preferably optimized taking into account the defined parameter comprising a flip angle to be generated and/or a characteristic of the slice to be excited, such as, for example, the slice profile, the slice position, the slice thickness and/or the slice orientation. If the optimization provides an increase in the duration of the excitation module and/or of the RF excitation pulse included in the excitation module while retaining the same flip angle that is to be generated, then the length of the RF excitation pulse can be increased, as a result of which the maximum amplitude and consequently the resulting SAR exposure for the examination subject can be reduced.

If the optimization provides for an increase in the duration of the excitation module and/or of the RF excitation pulse included in the excitation module given an optimization objective of a maximum flip angle to be generated, then the RF excitation pulse can be replaced by a different one which, given the same SAR exposure, is embodied for example to generate a higher flip angle due to the longer duration. A higher flip angle is advantageous within the scope of many MR control sequences since the signal-to-noise ratio correlates directly therewith.

For each RF excitation pulse available for selection, it is typically known with which defined parameter and which optimization objective said RF excitation pulse is compatible. The selection of an RF excitation pulse in the course of the optimization accordingly enables a precise fulfillment of optimization requirements. In particular, the slice profile can also be changed. By changing the duration of an RF excitation pulse included in the excitation module, it is possible to adjust an existing RF excitation pulse flexibly to a duration individually available during the optimization. This aspect can accordingly be used in a highly flexible manner.

An aspect of the method additionally comprises providing two RF excitation pulses, the optimization of the excitation module comprising selecting one RF excitation pulse of the two RF excitation pulses provided.

According to this aspect, there are preferably only two different excitation modules available, which comprise two different RF excitation pulses. The two provided RF excitation pulses are typically different in terms of their duration. The optimization of sequence modules having a usage time of the gradient coils of above-average intensity between excitation module and readout module with respect to time, in particular in the case of strong phase encoding gradients, typically comprises a selection of the shorter RF excitation pulse of the two RF excitation pulses provided.

The optimization of sequence modules having a usage time of the gradient coils of below-average intensity between excitation module and readout module with respect to time, in particular in the case of weak phase encoding gradients, typically comprises a selection of the longer RF excitation pulse of the two RF excitation pulses provided, which reduces the SAR exposure of the examination subject. The excitation module included in at least one sequence module may already comprise one of the two RF excitation pulses provided. The selection of an RF excitation pulse in the course of the optimization can then only comprise a confirmation of the RF excitation pulse present.

An aspect of the method provides that providing the two RF excitation pulses comprises calculating the two RF excitation pulses taking into account the optimization objective and/or the ascertained usage time for the at least two sequence modules. This aspect supports a particularly robust optimization of the excitation modules.

An aspect of the method provides that the optimization of the excitation module comprises adjusting a slice selection gradient included in the excitation module to the selected RF excitation pulse. By choosing a suitable slice selection gradient it can be ensured that the slice to be excited and/or the slice profile and/or the slice orientation is the same for different excitation modules. This aspect accordingly allows a combination of different excitation modules within an MR control sequence and in particular a combination of two sequence modules embodied having different excitation modules for the acquisition of MR data of the same slice of the examination region.

An aspect of the method provides that the usage time of the gradient coils is ascertained at least partially taking into account the at least one defined parameter provided. This enables the usage time to be ascertained in a particularly precise and predictable manner and consequently supports a robust optimization.

An aspect of the method provides that the MR control sequence comprises a plurality of sequence modules, the ascertained usage time of the gradient coils for at least 50%, preferably at least 60%, particularly preferably at least 70% of the plurality of sequence modules being determined by a phase-encoding magnetic field gradient included in the phase encoding module. According to this aspect, the usage time for a plurality of sequence modules is dependent on the phase encoding modules. The phase-encoding magnetic field gradients included in the phase encoding modules typically have vastly different gradient moments for the individual sequence modules, as a result of which there is a strong variation in the usage time and an optimization of the excitation module is particularly advantageous because optimization objectives can be effectively realized, in particular in the case of sequence modules relevant to the center of the raw data space.

An aspect of the method provides that more than 80%, preferably more than 90%, particularly preferably 100%, of the ascertained usage time of the gradient coils for at least one sequence module of the two sequence modules is determined by a phase-encoding magnetic field gradient included in the phase encoding module. Preferably, the phase-encoding magnetic field gradient included in the phase encoding module determines the usage time in the case of at least one sequence module of the two sequence modules. According to this aspect, there can be a particularly sharp difference between the usage times ascertained for the first sequence module and the second sequence module, as a result of which an optimization of the excitation module is particularly advantageous and optimization objectives can be realized in a flexible manner.

An aspect of the method provides that a usage time of the gradient coils is ascertained taking into account magnetic field gradients for compensating for a gradient moment generated by a slice selection gradient included in the excitation module and/or a magnetic field gradient for changing the phase start of a readout gradient included in the readout module and/or a phase-encoding magnetic field gradient. Preferably, a gradient pulse for compensating for a gradient moment generated by a slice selection gradient included in the excitation module is not included in the excitation module. Preferably, a gradient pulse for changing the phase start of a readout gradient included in the readout module is not included in the readout module. This aspect enables the relevant and/or significant magnetic field gradients occurring in the time interval between excitation module and readout module to be taken into account and consequently the usage time of the gradient coils to be ascertained in a compact and at the same time meaningful manner.

An aspect of the method provides that the duration of the optimized excitation module for the first sequence module of the at least two sequence modules which is embodied for acquiring MR data in a raw data space closer to the center of the raw data space is longer than the duration of the optimized excitation module for the second sequence module of the at least two sequence modules which is embodied for acquiring MR data further away from the center of the raw data space. The optimized excitation module of the first sequence module typically comprises an RF excitation pulse of longer duration and lower amplitude than an RF excitation pulse included in the optimized excitation module of the second sequence module. The optimized excitation module of the first sequence module typically comprises a slice selection gradient having lower amplitude than a slice selection gradient included in the optimized excitation module of the second sequence module. This aspect enables a particularly efficient optimization of the excitation module because optimization objectives can be effectively realized in particular in the case of usage times dominated by phase encoding modules for sequence modules relating to the center of the raw data space.

An aspect of the method additionally comprises checking the provided MR control sequence and/or the at least one defined parameter with regard to practicability of the optimization of the MR control sequence. If the result of the check is negative, an abort of the method can be initiated. The efficiency and/or practicability of the optimization depend in particular on the type of MR control sequence, for example whether the latter is gradient-echo-based or spin-echo-based. Thus, for example, an optimization can be discounted if the usage time of the gradient coils is dominated by magnetic field gradients for compensating for a gradient moment generated by a slice selection gradient included in the excitation module and/or by magnetic field gradients for changing the phase start of a readout gradient included in the readout module. In particular, an optimization can be discounted if the usage time for a majority of the sequence modules included in the MR control sequence is constant. This can also be dependent on the defined parameter, such as the examination region and/or a slice orientation, for example. This aspect accordingly enables an efficient optimization method since MR control sequences worthy of optimization can be selected in advance.

The disclosure further relates to an optimization unit comprising an input, an output, and a computing unit comprising an ascertainment unit and a determination unit. The optimization unit is embodied to perform a method for optimizing an MR control sequence.

Via the input, the optimization unit can be provided with an MR control sequence comprising at least two sequence modules and/or at least one defined parameter for the MR control sequence and/or an optimization objective and/or, optionally, RF excitation pulses. The optimization unit can be provided via the input with further functions, algorithms or parameters required in the method. The ascertainment unit is typically embodied to ascertain a usage time of the gradient coils between an excitation module and a readout module with respect to time for each of the at least two sequence modules. The determination unit is typically embodied to perform an optimization of the excitation modules separately for each of the at least two sequence modules taking into account the ascertained usage time for the corresponding sequence module and the at least one defined parameter with regard to the optimization objective. The optimized MR control sequence comprising the optimized excitation module and/or further results of an aspect of the method can be provided via the output.

Aspects of the optimization unit are embodied analogously to the aspects of the method. The optimization unit can comprise further control components that are necessary and/or advantageous for performing a method. Computer programs and other software by means of which the processor unit of the optimization unit automatically controls and/or executes a method workflow of a method can be stored in a memory unit of the optimization unit.

A computer program product can be loaded directly into a memory unit of a programmable optimization unit and/or computing unit and has program code means for performing a method when the computer program product is executed in the optimization unit, in particular in the computing unit of the optimization unit. As a result, the method can be performed quickly and in an identically repeatable and robust manner. The computer program product is configured in such a way that it is able to carry out the method steps by means of the optimization unit. In this case the optimization unit must satisfy the respective requirements, such as having a suitable random access memory, a suitable graphics card or a suitable logic unit, for example, so that the respective method steps can be carried out efficiently. The computer program product is stored for example on an electronically readable medium or held resident on a network or server, from where it can be downloaded into the processor of a local optimization unit and/or computing unit. Control information of the computer program product may also be stored on an electronically readable data medium. The control information of the electronically readable data medium can be embodied in such a way that it performs a method when the data medium is used in the computing unit of the optimization unit. Examples of electronically readable data media are a DVD, a magnetic tape or a USB stick on which electronically readable control information, in particular software, is stored. When said control information (software) is read from the data medium and loaded into an optimization unit and/or processor unit of an optimization unit, all aspects of the above-described methods can be performed.

The disclosure further relates to an electronically readable data medium on which a program is stored that is provided for performing a method for optimizing an MR control sequence.

The disclosure further relates to a magnetic resonance device comprising a control unit and an optimization unit. The magnetic resonance device is thus embodied to perform a method for optimizing an MR control sequence.

For this purpose, the control unit and/or the magnetic resonance device are/is connected to the optimization unit. The optimization unit may also be integrated into the control unit and/or the magnetic resonance device. The optimization unit may also be embodied separately from the control unit and/or the magnetic resonance device.

The magnetic resonance device is embodied to execute the optimized MR control sequence. In particular, the control unit is embodied to activate individual components of the magnetic resonance device by playing out an MR control sequence, in particular the optimized MR control sequence. Accordingly, the magnetic resonance device is embodied to implement an aspect of the method, which aspect provides that providing the optimized MR control sequence comprising the optimized excitation module comprises activating the magnetic resonance device in accordance with the optimized MR control sequence.

Aspects of the magnetic resonance device are embodied analogously to the aspects of the method. The magnetic resonance device can comprise further control components that are necessary and/or advantageous for performing a method. The magnetic resonance device can also be embodied to send control signals and/or to receive and/or to process control signals in order to perform a method. The optimization unit is preferably part of the control unit of the magnetic resonance device. Computer programs and other software by means of which the processor unit of the optimization unit automatically controls and/or executes a method workflow of a method can be stored in a memory unit of the optimization unit.

The advantages of the optimization unit, the magnetic resonance device, the computer program product and the electronically readable data medium substantially correspond to the advantages of the method for optimizing an MR control sequence, which are presented in detail hereinabove. Features, advantages or alternative aspects mentioned in this context may equally be applied also to the other claimed subject matters, and vice versa.

BRIEF DESCRIPTION OF THE DRAWINGS

Further advantages, features and specific details of the disclosure will become apparent from the exemplary aspects described in the following, as well as with reference to the drawings, in which.

DETAILED DESCRIPTION

Figure 1:
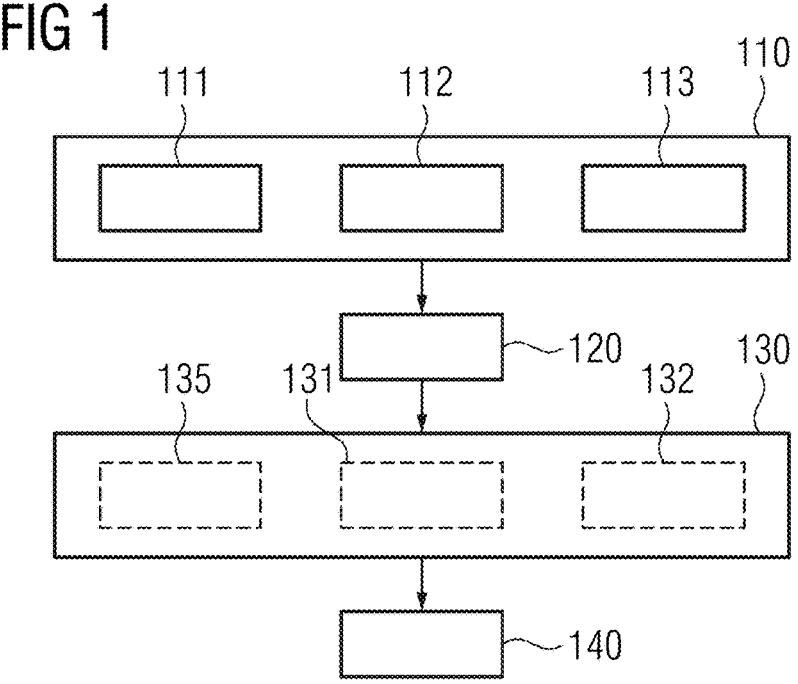
FIG. 1 shows a flowchart of a first aspect of a method in accordance with aspects of the disclosure.

FIG. 1 shows a flowchart of a first aspect of a method for optimizing an MR control sequence embodied for acquiring MR data of an examination subject by means of a magnetic resonance device comprising gradient coils. The method starts at method step 110, providing data required in the method. In method step 110, the data is provided preferably using the input 34 of the optimization unit 33. In particular, method step 110 in conjunction with method step 111 comprises providing an MR control sequence comprising at least two sequence modules M1, M2, each having an excitation module Ma1, Ma2, a phase encoding module Mp1, Mp2 and a readout module Mr1, Mr2, the phase encoding module Mp1, Mp2 in each case being arranged between excitation module Ma1, Ma2 and readout module Mr1, Mr2 with respect to time. Method step 110 in conjunction with method step 112 also comprises providing at least one defined parameter for the MR control sequence and, in conjunction with method step 113, providing an optimization objective. In method step 120, a usage time of the gradient coils between excitation module Ma1, Ma2 and readout module Mr1, Mr2 with respect to time is ascertained for each of the at least two sequence modules M1, M2. Method step 120 is preferably performed by the ascertainment unit 36 of the optimization unit 33. Optionally, method step 120 can be performed at least in part taking into account the at least one defined parameter provided in method step 112.

Method step 130 comprises optimizing the excitation modules Ma1, Ma2 separately for each of the at least two sequence modules M1, M2 taking into account the ascertained usage time for the corresponding sequence module M1, M2 and the at least one defined parameter with regard to the optimization objective. Method step 130 is preferably carried out by the determination unit 37 of the optimization unit 33. Method step 140 comprises providing the optimized MR control sequence comprising the optimized excitation module Ma1', Ma2'. The providing in method step 140 is preferably realized using the output 35 of the optimization unit 33.

Method step 130, optimizing the excitation module Ma1, Ma2, can comprise, in conjunction with method step 131, selecting a new RF excitation pulse RF1, RF2 included in the excitation module Ma1, Ma2 and/or, in conjunction with method step 132, adjusting the duration of an RF excitation pulse RF1, RF2 included in the excitation module Ma1, Ma2. Alternatively and/or in addition, method step 130 can optionally comprise, in conjunction with method step 135, checking the provided MR control sequence and/or the at least one defined parameter with regard to practicability of the optimization of the MR control sequence.

Figure 2:
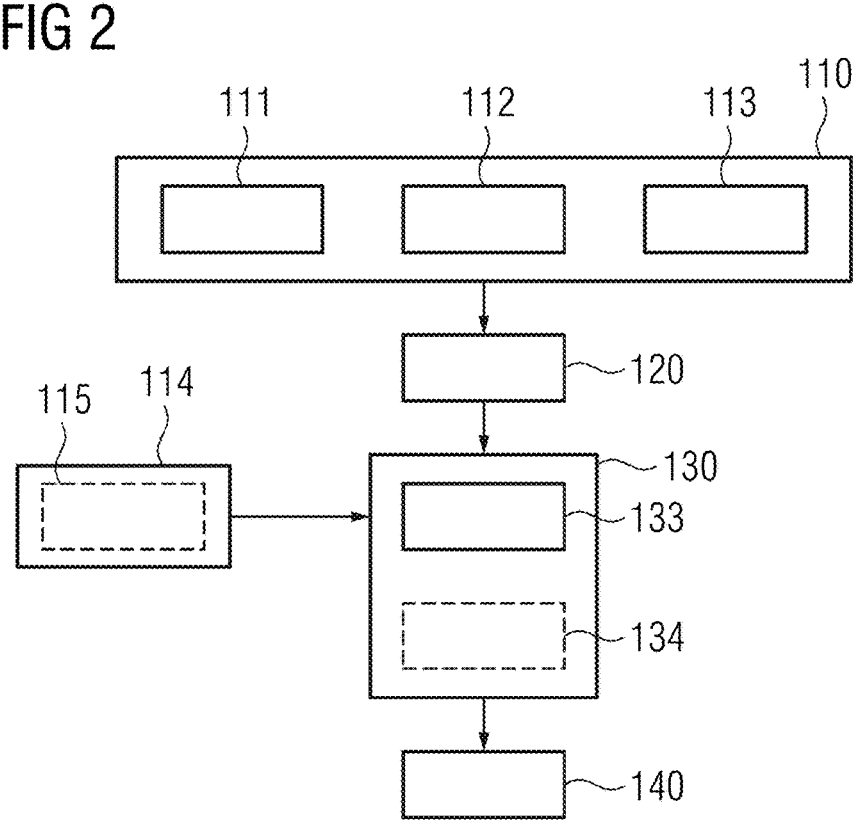
FIG. 2 shows a flowchart of a second aspect of a method in accordance with aspects of the disclosure.

FIG. 2 shows a flowchart of a second aspect of a method. The second aspect differs from the mandatory steps of the first aspect by method step 114, providing two RF excitation pulses RF1*, RF2*, and method step 133, selecting one RF excitation pulse of the two provided RF excitation pulses RF1*, RF2* in the course of the optimization of the excitation module Ma1, Ma2 according to method step 130. The RF excitation pulse selected from the provided RF excitation pulses RF1*, RF2* and/or the RF excitation pulse included in the optimized excitation module Ma1', Ma2' are/is designated in the following by RF1', RF2'. Method step 130 can comprise, optionally in conjunction with method step 134, adjusting a slice selection gradient Mas1, Mas2 included in the excitation module Ma1, Ma2 to the selected RF excitation pulse RF1', RF2'.

The RF excitation pulses RF1*, RF2* provided in method step 114 typically differ in terms of their duration. The providing of two RF excitation pulses RF1*, RF2* in method step 114 can comprise, in conjunction with method step 115, calculating the two RF excitation pulses RF1*, RF2* taking into account the optimization objective and/or the ascertained usage time for the at least two sequence modules M1, M2.

Figure 3:
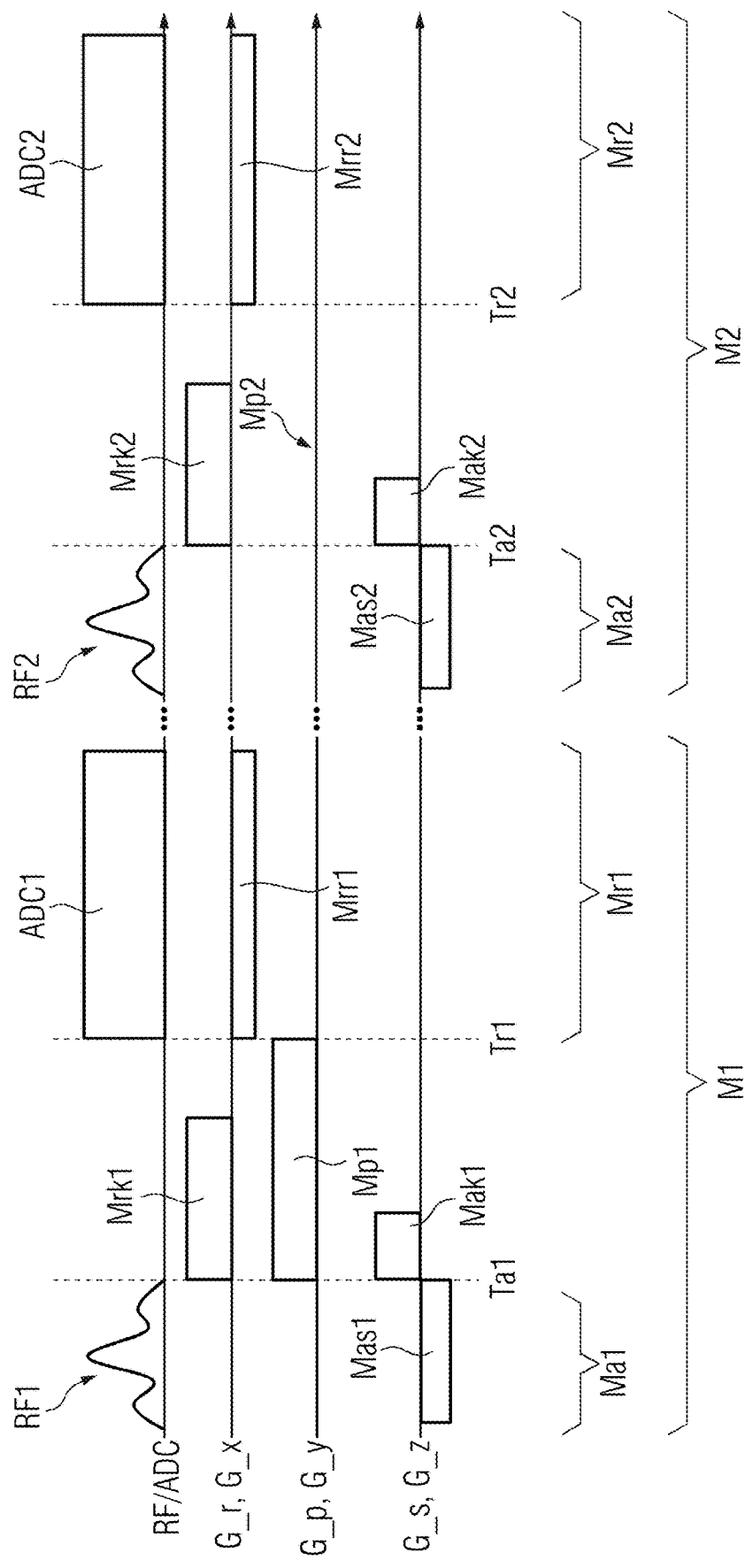
FIG. 3 shows a timing diagram of an MR control sequence prior to its optimization in accordance with aspects of the disclosure.
Figure 4:
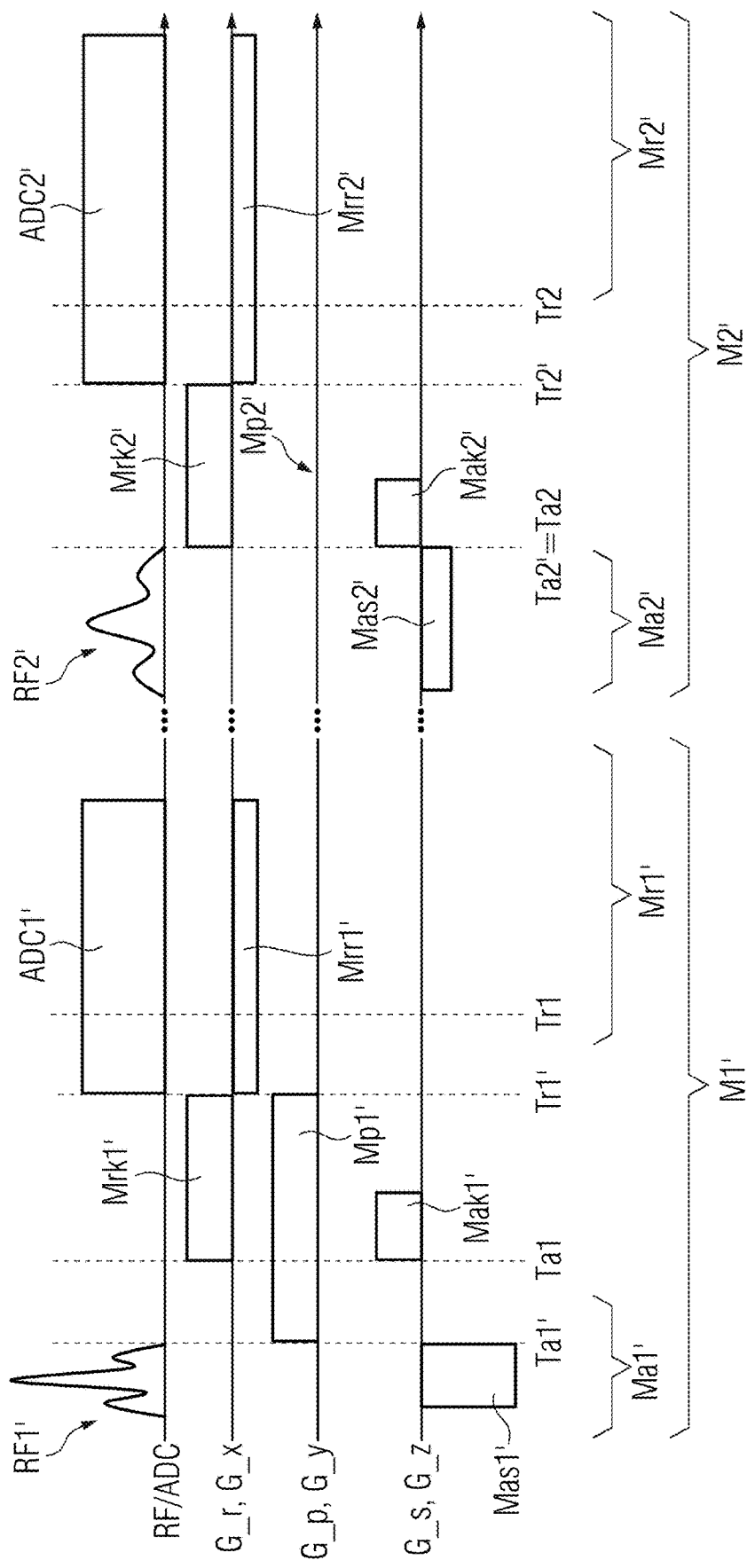
FIG. 4 shows a timing diagram of an optimized MR control sequence in accordance with aspects of the disclosure.

FIG. 3 shows a timing diagram of an MR control sequence prior to its optimization and FIG. 4 shows a timing diagram of said MR control sequence after optimization. In the horizontal direction, the time characteristic is indicated for the RF pulses (RF), or, as the case may be, the activity of the analog-to-digital converter (ADC) required for capturing MR signals, for the magnetic field gradient in the readout direction (G_r), the magnetic field gradient in the phase encoding direction (G_p), and the magnetic field gradient in the slice selection direction (G_s). The exceptional case is illustrated whereby the cited directions correspond to the physical axes x, y, z of the gradient coil unit 19 such that the magnetic field gradient in the readout direction (G_r) can be generated by the gradient coil G_x active in the x-direction, the magnetic field gradient in the phase encoding direction (G_p) can be generated by the gradient coil G_y active in the y-direction, and the magnetic field gradient in the slice selection direction (G_s) can be generated by the gradient coil G_z active in the z-direction. Generally, the readout direction G_r, the phase encoding direction G_p and the slice selection direction G_s do not coincide with the physical axes x, y, z, and the phase encoding module Mp1, Mp2, for example, would be generated by at least two physical axes of the three physical axes x, y, z. However, the optimization according to method step is performed taking into account the usage time ascertained for the gradient coils G_x, G_y, G_z, i.e. based on the physical axes x, y, z. For the sake of simplicity, the magnetic field gradients are shown with an infinitely high slew rate. In reality, the magnetic field gradients exhibit a trapezoidal waveform.

The MR control sequence shown in FIG. 3 comprises two sequence modules M1, M2, each having an excitation module Ma1, Ma2, a phase encoding module Mp1, Mp2 and a readout module Mr1, Mr2.

The first excitation module Ma1 of the first sequence module M1 comprises a first RF excitation pulse RF1 and a first slice selection gradient Mas1. The temporal end of the first excitation module Ma1 is marked by Ta1. The first readout module Mr1 comprises a first ADC activity ADC1 and a first readout gradient Mrr1 switched simultaneously herewith. The temporal start of the first readout module Mr1 is marked by Tr1. The first phase encoding module Mp1 comprises a first magnetic field gradient in the phase encoding direction G_p. In the case illustrated, the first phase encoding module Mp1 comprises the magnetic field gradient of the MR control sequence having maximum amplitude, as a result of which the first sequence module M1 is embodied to acquire MR data at the periphery of the raw data space, i.e. at a maximum spacing from the center of the raw data space.

The first magnetic field gradient Mak1 for compensating for a gradient moment generated by the first slice selection gradient Mas1 is not included in the first excitation module Ma1 and is arranged with respect to time between the end Ta1 of the first excitation module Ma1 and the start Tr1 of the first readout module Mr1. The first magnetic field gradient Mrk1 for changing the phase start of the first readout gradient Mrr1 is not included in the first readout module Mr1 and is arranged with respect to time between the end Ta1 of the first excitation module Ma1 and the start Tr1 of the first readout module Mr1.

The second excitation module Ma2 of the second sequence module M2 comprises a second RF excitation pulse RF2 and a second slice selection gradient Mas2. The temporal end of the second excitation module Ma2 is marked by Ta2. The second readout module Mr2 comprises a second ADC activity ADC2 and a second readout gradient Mrr2 switched simultaneously herewith. The temporal start of the second readout module Mr2 is marked by Tr2.

The second phase encoding module Mp2 comprises a second magnetic field gradient in the phase encoding direction G_p. In the case illustrated, the second phase encoding module Mp2 comprises a magnetic field gradient of amplitude 0, as a result of which the second sequence module M2 is embodied to acquire MR data in the center of the raw data space.

The second magnetic field gradient Mak2 for compensating for a gradient moment generated by the second slice selection gradient Mas2 is not included in the second excitation module Ma2 and is arranged with respect to time between the end Ta2 of the second excitation module Ma2 and the start Tr2 of the second readout module Mr2. The second magnetic field gradient Mrk2 for changing the phase start of the second readout gradient Mrr2 is not included in the second readout module Mr2 and is arranged with respect to time between the end Ta2 of the second excitation module Ma2 and the start Tr2 of the second readout module Mr2.

In the case illustrated, the only difference between the first sequence module M1 and the second sequence module M2 is the intensity of the magnetic field gradient included in the respective phase encoding module Mp1, Mp2.

For the first sequence module M1, the gradient coils G_x, G_y, G_z are under continuous load in the time between first excitation module Ma1 and first readout module Mr1, i.e. between Ta1 and Tr1. The usage time of the gradient coils G_x, G_y, G_z between first excitation module Ma1 and first readout module Mr1 with respect to time therefore corresponds 100% to the period of time between Ta1 and Tr1. In particular, the first phase encoding module Mp1 imposes a 100% load on the gradient coil G_p, G_y during this time, as a result of which the ascertained usage time is determined completely by the duration of the first phase encoding module Mp1. The usage time of the gradient coils G_x, G_y, G_z is therefore dominated in the first sequence module M1 by the magnetic field gradient of the first phase encoding module Mp1.

For the second sequence module M2, the gradient coils G_x, G_y, G_z are under load only by Mrk2 and Mak2 in the time between second excitation module Ma2 and second readout module Mr2, i.e. between Ta2 and Tr2. In the case illustrated, the usage time of the gradient coils G_x, G_y, G_z between second excitation module Ma2 and second readout module Mr2 with respect to time corresponds to approx. 70% of the period of time Ta2 and Tr2.

The usage time of the gradient coils G_x, G_y, G_z is therefore dominated in the second sequence module M2 by the second magnetic field gradient Mak2 for compensating for the gradient moment generated by the second slice selection gradient Mas2 and/or the second magnetic field gradient Mrk2 for changing the phase start of the second readout gradient Mrr2.

The optimized form shown in FIG. 4 of the MR control sequence shown in FIG. 3 comprises an optimized first sequence module M1' and an optimized second sequence module M2'.

The optimized first sequence module M1' differs from the first sequence module M1 by an optimized first RF excitation pulse RF1' which is shorter than the RF excitation pulse RF1 included in the first excitation module Ma1. Similarly, the optimized first excitation module Ma1' has an optimized first slice selection gradient Mas1' whose amplitude has been increased compared to Mas1 and adjusted to the shorter duration of the optimized first RF excitation pulse RF1'. Because of the shortened duration of the optimized first excitation module Ma1', its end Ta1' is earlier in time compared to Ta1, such that the optimized first phase encoding module Mp1' can also start at time point Ta1', i.e. earlier. Apart from the earlier start time, the optimized first phase encoding module Mp1' is unchanged compared to the first phase encoding module Mp1. Having been brought forward, the optimized first phase encoding module Mp1' enables an earlier start of the optimized first readout module Mr1', which, apart from the earlier start at time point Tr1', is unchanged compared to the first readout module Mr1. The period of time between the optimized first excitation module Ma1' and the optimized first readout module Mr1', i.e. between Ta1' and Tr1', is occupied completely, in particular by the optimized first phase encoding module Mp1'.

The optimized second sequence module M2' differs from the second sequence module M2 by an earlier start of the optimized second readout module Mr2', which, apart from the earlier start at time point Tr2', is unchanged compared to the second readout module Mr2. The period of time between the optimized second excitation module Ma2' and the optimized second readout module Mr2', i.e. between Ta2' and Tr2', is taken up completely, in particular by the optimized second magnetic field gradient Mrk2' for changing the phase start of the second readout gradient Mrr2'.

The echo time, defined by the period of time between the start of the optimized excitation module Ma1', Ma2' and the start of the optimized readout module Mr1', Mr2', is of equal size for the first optimized sequence module M1' and the second optimized sequence module M2'.

Figure 5:
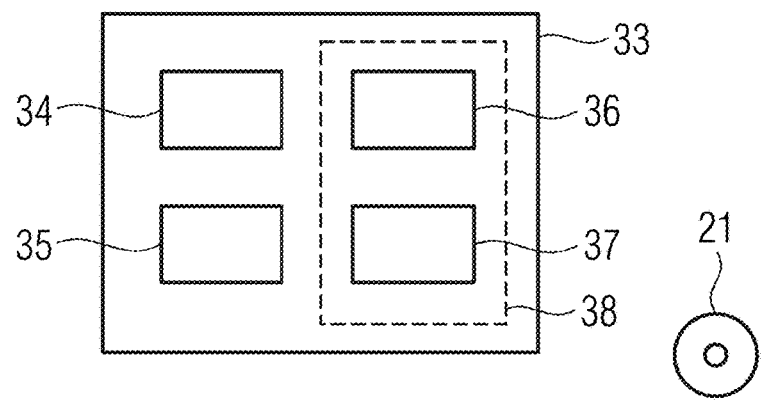
FIG. 5 shows an optimization unit in a schematic view in accordance with aspects of the disclosure.

FIG. 5 shows an optimization unit 33 in a schematic view. The optimization unit 33 comprises an input 34, an output 35, and a computing unit 38 comprising an ascertainment unit 36 and a determination unit 37. The optimization unit 33 is furthermore configured to perform a method for optimizing an MR control sequence. For this purpose, the optimization unit 33 comprises computer programs and/or software that can be loaded directly into a memory unit (not shown in more detail) of the optimization unit 33 and have program means for performing a method for optimizing an MR control sequence when the computer programs and/or software are executed in the optimization unit 33. For this purpose, the optimization unit 33 has a processor (not shown in more detail) which is configured to run the computer programs and/or software. Alternatively hereto, the computer programs and/or software can also be stored on an electronically readable data medium 21 embodied separately from the optimization unit 33, in which case a data access by the optimization unit 33 to the electronically readable data medium 21 can be performed via a data network.

A method for optimizing an MR control sequence may also be present in the form of a computer program product which implements the method on the optimization unit 33, in particular on the computing unit 38, when it is executed on the optimization unit 33. Similarly, an electronically readable data medium 21 may be present on which electronically readable control information is stored which comprises at least one such computer program product as just described and is embodied in such a way that it carries out the described method when the data medium 21 is used in an optimization unit 33.

Figure 6:
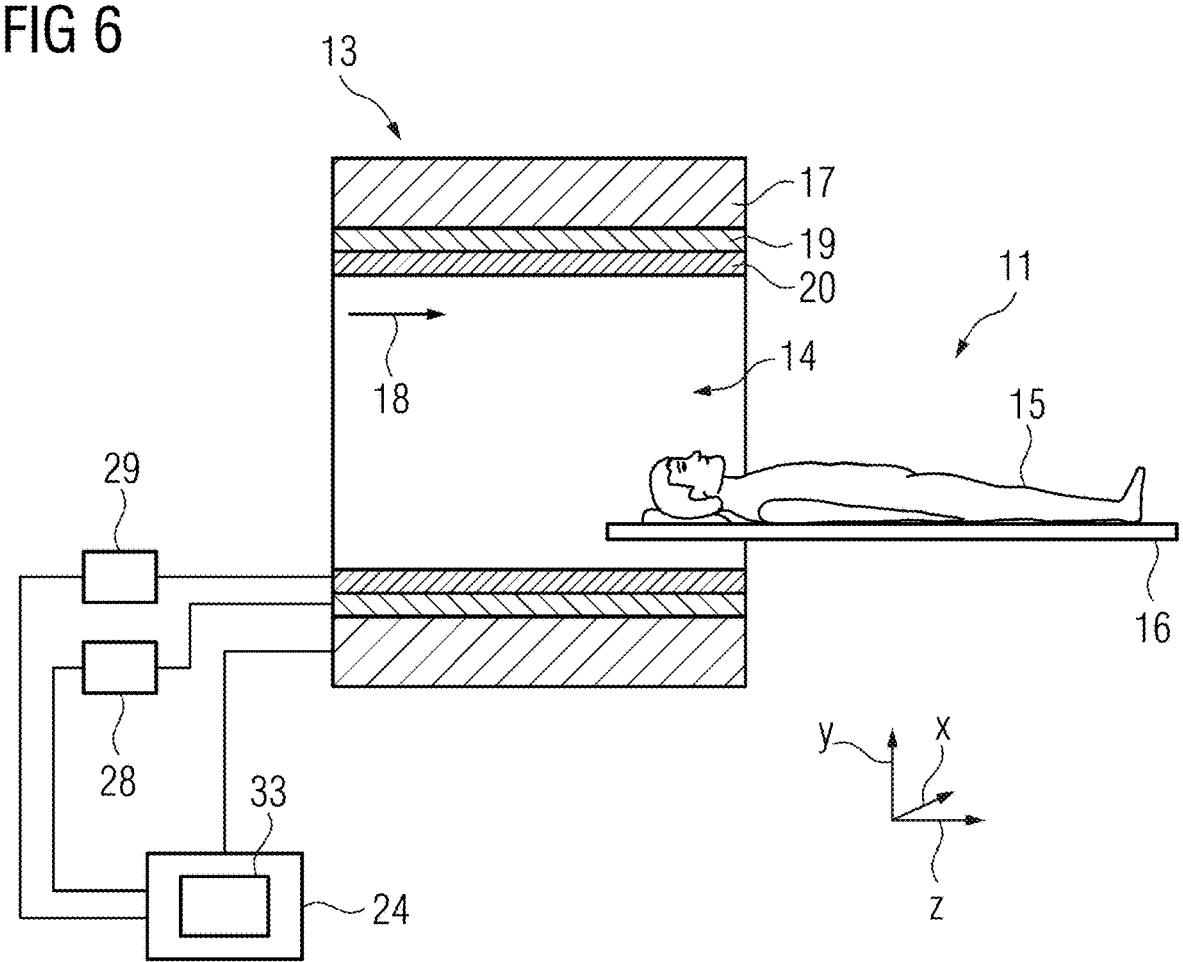
FIG. 6 shows a magnetic resonance device in a schematic view in accordance with aspects of the disclosure.

FIG. 6 shows a magnetic resonance device 11 for performing a method in a schematic view. The magnetic resonance device 11 comprises a detector unit formed by a magnet unit 13 and having a main magnet 17 for generating a strong and in particular constant main magnetic field 18. In addition, the magnetic resonance device 11 comprises a cylinder-shaped patient receiving zone 14 for accommodating a patient 15, the patient receiving zone 14 being cylindrically enclosed by the magnet unit 13 in a circumferential direction. The patient 15 can be introduced into the patient receiving zone 14 by means of a patient support and positioning device 16 of the magnetic resonance device 11. For this purpose, the patient support and positioning device 16 has a patient table which is arranged so as to be movable inside the magnetic resonance device 11.

The magnet unit 13 additionally features a gradient coil unit 19 that is used for spatial encoding during an imaging session. The gradient coil unit 19 typically comprises three gradient coils $G\_x$, $G\_y$, $G\_z$, one gradient coil of the three gradient coils $G\_x$, $G\_y$, $G\_z$ being embodied in each case for generating one magnetic field gradient of the three magnetic field gradients in one of the three spatial directions x, y, z. The gradient coil unit 19 is driven by means of a gradient control unit 28. The magnet unit 13 further comprises a radiofrequency antenna unit 20 which, in the case shown, is embodied as a whole-body coil permanently integrated in the magnetic resonance device 11, and a radiofrequency antenna control unit 29 for exciting a polarization which becomes established in the main magnetic field 18 generated by the main magnet 17. The radiofrequency antenna unit 20 is driven by the radiofrequency antenna control unit 29 and radiates high-frequency radiofrequency pulses into an examination chamber that is substantially formed by the patient receiving zone 14.

The magnetic resonance device 11 comprises a control unit 24 for controlling the main magnet 17, the gradient control unit 28 and the radiofrequency antenna control unit 29. The control unit 24 is responsible for the centralized control of the magnetic resonance device 11, such as for executing MR control sequences, for example. In addition, the control unit 24 comprises a reconstruction unit (not shown in more detail) for reconstructing medical image data acquired during the magnetic resonance examination. The control unit 24 may comprise the gradient control unit 28 and/or the radiofrequency antenna control unit 29.

The control unit 24 also comprises an optimization unit 33. The optimization unit 33 is furthermore configured to perform a method for optimizing an MR control sequence. For this purpose, the optimization unit 33 comprises computer programs and/or software that can be loaded directly into a memory unit (not shown in more detail) of the optimization unit 33 and have program means for performing a method for optimizing an MR control sequence when the computer programs and/or software are executed in the optimization unit 33. For this purpose, the optimization unit 33 has a processor (not shown in more detail) which is configured for running the computer programs and/or software.

The illustrated magnetic resonance device 11 may of course include further components that are ordinarily contained in magnetic resonance devices 11. The general principle of operation of a magnetic resonance device 11 is furthermore known to the person skilled in the art, so a detailed description of the further components will be dispensed with. The magnetic resonance device 11 is accordingly configured to perform a method in conjunction with the optimization unit 33.

Although the disclosure has been illustrated and described in greater detail on the basis of the preferred exemplary aspects, the disclosure is not limited by the disclosed examples and other variations may be derived herefrom by the person skilled in the art without leaving the scope of protection of the disclosure.

The invention claimed is:

1. A method for optimizing an MR control sequence embodied to acquire magnetic resonance (MR) data of an examination subject by means of a magnetic resonance device comprising gradient coils, the method comprising:
   providing an MR control sequence comprising at least two sequence portions, each having an excitation portion, a phase encoding portion and a readout portion, wherein the phase encoding portion is in each case arranged between the excitation portion and the readout portion with respect to time;
   providing at least one defined parameter for the MR control sequence;
   providing an optimization objective;
   ascertaining a usage time of the gradient coils between the excitation portion and the readout portion with respect to time for each of the at least two sequence portions;
   optimizing the excitation portions for each of the at least two sequence portions taking into account the ascertained usage time for the corresponding sequence portion and the at least one defined parameter with regard to the optimization objective; and
   providing the optimized MR control sequence comprising the optimized excitation portions,
   wherein the duration of the optimized excitation portion for a first sequence portion of the at least two sequence portions, which is embodied for acquiring MR data in a raw data space closer to the center of the raw data space, is longer than the duration of the optimized excitation portion for a second sequence portion of the at least two sequence portions, which is embodied for acquiring MR data further away from the center of the raw data space.

2. The method as claimed in claim 1, wherein the defined parameter comprises at least one of the following characteristics: echo time, repetition time, slice thickness, slice position, slice profile, slice orientation, examination region, amplitude of a magnetic field gradient, and flip angle to be generated by the excitation portion.

3. The method as claimed in claim 1, wherein the optimization objective relates to: an SAR exposure of the examination subject, and/or a total duration of the sequence portion, and/or a ratio of echo time to repetition time, and/or a flip angle to be generated by an excitation portion, and/or allocation of a predetermined duration for the excitation portion and/or an extreme value for one of the cited optimization objectives.

4. The method as claimed in claim 1, wherein providing the optimization objective comprises calculating an extreme value for an SAR exposure of the examination subject, and/or a total duration of the sequence portion, and/or a ratio of echo time to repetition time taking into account the at least one defined parameter, and/or a flip angle to be generated by an excitation portion, and/or allocation of a predetermined duration for the excitation portion, and/or a maximum loading of at least one component of the magnetic resonance device, and/or of the ascertained usage time for the at least two sequence portions.

5. The method as claimed in claim 1, wherein the optimization of the excitation portion comprises selecting a new RF excitation pulse included in the excitation portion, and/or adjusting the duration of an RF excitation pulse included in the excitation portion.

6. The method as claimed in claim 5, wherein the optimization of the excitation portion comprises adjusting a slice selection gradient included in the excitation portion to the selected RF excitation pulse.

7. The method as claimed in claim 1, further comprising:
providing two RF excitation pulses, wherein the optimization of the excitation portion comprises selecting one RF excitation pulse of the two RF excitation pulses provided.

8. The method as claimed in claim 7, wherein the providing the two RF excitation pulses comprises calculating the two RF excitation pulses taking into account the optimization objective and/or the ascertained usage time for the at least two sequence portions.

9. The method as claimed in claim 1, wherein the MR control sequence comprises a plurality of sequence portions, and wherein the ascertained usage time of the gradient coils for at least 50% of the plurality of sequence portions is determined by a phase-encoding magnetic field gradient included in the phase encoding portion.

10. The method as claimed in claim 1, wherein more than 80% of the ascertained usage time of the gradient coils for at least one sequence portion of the two sequence portions is determined by a phase-encoding magnetic field gradient included in the phase encoding portion.

11. The method as claimed in claim 1, wherein a usage time of the gradient coils is ascertained taking into account magnetic field gradients for compensating for a gradient moment generated by a slice selection gradient included in the excitation portion, and/or a magnetic field gradient for changing the phase start of a readout gradient included in the readout portion, and/or a phase-encoding magnetic field gradient.

12. The method as claimed in claim 1, further comprising:
checking the provided MR control sequence and/or the at least one defined parameter with regard to practicability of the optimization of the MR control sequence.

13. A magnetic resonance device comprising a controller and an optimization processor comprising a compute processor which is configured to perform a method for optimizing an MR control sequence as claimed in claim 1.

14. A non-transitory computer readable medium having stored thereon software instructions that, when executed by a programmable optimization processor, cause the programmable optimization processor to perform a method for optimizing an MR control sequence as claimed in claim 1.

* * * * *